US010434075B2

(12) United States Patent
Cox et al.

(10) Patent No.: US 10,434,075 B2
(45) Date of Patent: Oct. 8, 2019

(54) FKBP52 SPECIFIC ANDROGEN RECEPTOR INHIBITOR, MJC13, FOR USE IN TREATING BREAST CANCER

(71) Applicants: Marc B. Cox, El Paso, TX (US); Jennifer Richer, Denver, CO (US)

(72) Inventors: Marc B. Cox, El Paso, TX (US); Jennifer Richer, Denver, CO (US)

(73) Assignees: THE BOARD OF REGENTS OF THE UNIVERSITY OF TEXAS SYSTEM, Austin, TX (US); THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 15/623,775

(22) Filed: Jun. 15, 2017

(65) Prior Publication Data
US 2017/0360725 A1    Dec. 21, 2017

Related U.S. Application Data

(60) Provisional application No. 62/350,383, filed on Jun. 15, 2016.

(51) Int. Cl.
| | |
|---|---|
| *A61K 31/167* | (2006.01) |
| *A61K 31/513* | (2006.01) |
| *A61K 31/337* | (2006.01) |
| *A61K 31/17* | (2006.01) |
| *A61K 31/138* | (2006.01) |
| *A61K 31/704* | (2006.01) |
| *A61K 31/675* | (2006.01) |
| *A61K 31/555* | (2006.01) |
| *A61K 31/565* | (2006.01) |
| *A61K 31/685* | (2006.01) |
| *A61K 45/06* | (2006.01) |
| *A61K 31/4196* | (2006.01) |
| *A61K 31/5685* | (2006.01) |

(52) U.S. Cl.
CPC .......... *A61K 31/167* (2013.01); *A61K 31/138* (2013.01); *A61K 31/17* (2013.01); *A61K 31/337* (2013.01); *A61K 31/4196* (2013.01); *A61K 31/513* (2013.01); *A61K 31/555* (2013.01); *A61K 31/565* (2013.01); *A61K 31/5685* (2013.01); *A61K 31/675* (2013.01); *A61K 31/704* (2013.01); *A61K 45/06* (2013.01)

(58) Field of Classification Search
CPC .. A61K 31/167; A61K 31/513; A61K 31/337; A61K 31/17; A61K 31/138; A61K 31/704; A61K 31/675; A61K 31/555; A61K 31/565; A61K 31/685; A61K 45/06
USPC ........................................................ 514/613
See application file for complete search history.

(56) References Cited

U.S. PATENT DOCUMENTS

2016/0030369 A1* 2/2016 Xie ...................... A61K 9/0019
424/450

OTHER PUBLICATIONS

D'Amato et al., Molecular Cancer Research (2016), 14(11), 1054-1067.*
Miles et al., The Oncologist, 2002, 7(suppl 6): 13-19.*
Cochrane et al., abstract, 2012, https://archive.is/20130223124357/http://cancerres.aacrjournals.org/cgi/content/meeting_abstract/72/24_MeetingAbstracts/P2-14-02.*
Cochrane et al., Cancer Reearch, 2012, 72(24 suppl 3).*
Aromatase Inhibitor—Wikipedia, 2018, https://en.wikipedia.org/wiki/Aromatase_inhibitor.*
Tamoxifen—Wikipedia, 2018, https://en.wikipedia.org/wiki/Tamoxifen.*
Breat cancer—Wikipedia, 2018, https://en.wikipedia.org/wiki/Breast_cancer.*
BreastCancerCure, 2018, http://www.breastcancer.org/questions/cancer_free.*
BreastCancerPrevention, 2018, https://www.cancer.org/cancer/breast-cancer/risk-and-prevention.html.*
Agoff, et al., (2003) Androgen receptor expression in estrogen receptor-negative breast cancer. Immunohistochemical, clinical, and prognostic associations. *Am J Clin Pathol* 120, 725-731.
Bergh, et al., (2012) FACT: An Open-Label Randomized Phase III Study of Fulvestrant and Anastrozole in Combination Compared With Anastrozole Alone as First-Line Therapy for Patients With Receptor-Positive Postmenopausal Breast Cancer. *J Clin Oncol*, vol. 30, No. 16, pp. 1919-1925.
Carroll, et al., (2005) Chromosome-wide mapping of estrogen receptor binding reveals long-range regulation requiring the forkhead protein FoxA1. *Cell* 122, 33-43.
Cauley, et al., (1999) Elevated serum estradiol and testosterone concentrations are associated with a high risk for breast cancer. Study of Osteoporotic Fractures Research Group. *Ann Intern Med* 130, 270-277.
Cochrane, et al., (2014) Role of the androgen receptor in breast cancer and preclinical analysis of enzalutamide. *Breast Cancer Res* 16, R7.
Collins, et al., (2011) Androgen receptor expression in breast cancer in relation to molecular phenotype: results from the Nurses' Health Study. *Mod Pathol* 24, 924-931.
De Amicis, et al., (2010) Androgen receptor overexpression induces tamoxifen resistance in human breast cancer cells. *Breast Cancer Res Treat* 121, 1-11.

(Continued)

*Primary Examiner* — Sun Jae Yoo
(74) *Attorney, Agent, or Firm* — Norton Rose Fulbright US LLP

(57) ABSTRACT

Embodiments of the current invention include methods and compositions for treating breast cancer by administering an effective amount of MJC13 to a subject in need thereof.

6 Claims, 3 Drawing Sheets

(56) References Cited

OTHER PUBLICATIONS

De Leon, et al., (2011) Targeting the regulation of androgen receptor signaling by the heat shock protein 90 cochaperone FKBP52 in prostate cancer cells. *Proc Natl Acad Sci U S A* 108, 11878-11883.

Gallicchio, et al., (2011) Androgens and musculoskeletal symptoms among breast cancer patients on aromatase inhibitor therapy. *Breast Cancer Res Treat*, vol. 130, No. 2, pp. 569-577.

Guedj, et al., (2012) A refined molecular taxonomy of breast cancer. *Oncogene* 31, 1196-1206.

Harvell, et al., (2008) Estrogen regulated gene expression in response to neoadjuvant endocrine therapy of breast cancers: tamoxifen agonist effects dominate in the presence of an aromatase inhibitor. *Breast Cancer Res Treat*, vol. 112, No. 3, pp. 489-501.

Harvell, et al., (2008) Molecular signatures of neoadjuvant endocrine therapy for breast cancer: characteristics of response or intrinsic resistance. *Breast Cancer Res Treat*, vol. 112, pp. 475-488.

Hu, et al., (2011) Androgen receptor expression and breast cancer survival in postmenopausal women. *Clin Cancer Res* 17, 1867-1874.

Hurtado, et al., (2011) FOXA1 is a key determinant of estrogen receptor function and endocrine response. *Nat Genet* 43, 27-33.

Kuenen-Boumeester, et al., (1996) The clinical significance of androgen receptors in breast cancer and their relation to histological and cell biological parameters. *Eur J Cancer* 32A, 1560-1565.

Lehmann, et al., (2011) Identification of human triple-negative breast cancer subtypes and preclinical models for selection of targeted therapies. *J Clin Invest* 121, 2750-2767.

Liang, et al., (2014) Quantification of a New Anti-Cancer Molecule MJC13 Using a Rapid, Sensitive, and Reliable Liquid Chromatography-Tandem Mass Spectrometry Method. *American Journal Modern Chromatography* 1, 1-11.

Liang, et al., (2016) Solution formulation development and efficacy of MJC13 in a preclinical model of castration-resistant prostate cancer. *Pharm Dev Technol*, vol. 21, No. 1, pp. 121-126.

Lupien et al., (2009) Cistromics of hormone-dependent cancer. *Endocr Relat Cancer* 16, 381-389.

Migliaccio, et al., (2000) Steroid-induced androgen receptor-oestradiol receptor beta-Src complex triggers prostate cancer cell proliferation. *Embo J* 19, 5406-5417.

Mouridsen, et al., (2003) Phase III study of letrozole versus tamoxifen as first-line therapy of advanced breast cancer in postmenopausal women: analysis of survival and update of efficacy from the International Letrozole Breast Cancer Group. *J Clin Oncol* 21, 2101-2109.

Need, et al., (2012) Research resource: interplay between the genomic and transcriptional networks of androgen receptor and estrogen receptor alpha in luminal breast cancer cells. *Mol Endocrinol* 26, 1941-1952.

Panet-Raymond, et al., (2001) Characterization of intracellular aggregates using fluorescently-tagged polyglutamine-expanded androgen receptor. *Neurotox Res* 3, 259-275.

Park, et al., (2010) Expression of androgen receptors in primary breast cancer. *Ann Oncol* 21, 488-492.

Peters, et al., (2009) Androgen receptor inhibits estrogen receptor-alpha activity and is prognostic in breast cancer. *Cancer Res* 69, 6131-6140.

Rechoum, et al., (2014) AR collaborates with ERalpha in aromatase inhibitor-resistant breast cancer. *Breast Cancer Res Treat* 147, 473-485.

Robinson, et al., (2011) Androgen receptor driven transcription in molecular apocrine breast cancer is mediated by FoxA1. *Embo J* 30, 3019-3027.

Soreide, et al., (1992) Androgen receptors in operable breast cancer: relation to other steroid hormone receptors, correlations to prognostic factors and predictive value for effect of adjuvant tamoxifen treatment. *Eur J Surg Oncol* 18, 112-118.

Zeleniuch-Jacquotte, et al., (2012) Premenopausal serum androgens and breast cancer risk: a nested case-control study. *Breast Cancer Res* 14, R32.

Zhang, et al., (2010) CCCTC-binding factor acts upstream of FOXA1 and demarcates the genomic response to estrogen. *J Biol Chem* 285, 28604-28613.

\* cited by examiner

FKBP52 SPECIFIC ANDROGEN RECEPTOR INHIBITOR, MJC13, FOR USE IN TREATING BREAST CANCER

PRIORITY PARAGRAPH

This application claims priority to U.S. Application No. 62/350,383 filed Jun. 15, 2016, which is incorporated herein by reference in its entirety.

STATEMENT REGARDING FEDERALLY FUNDED RESEARCH

This invention was made with government support under BC120183 W81XWH-13-1-0090 and 1 R01 CA187733-01A1 awarded by the Department of Defense and National Institutes of Health (NIH), respectively. The government has certain rights in the invention.

BACKGROUND

Androgens are a major stimulator of prostate tumor growth and all current therapies act as classic antagonists by competing with androgens for binding the androgen receptor (AR) hormone binding pocket. This mechanism of action exploits the dependence of AR for hormone activation and current treatment options are essentially ineffective once androgen-dependence is lost. Thus, drugs that target novel surfaces on AR and/or novel AR regulatory mechanisms are promising additions for the treatment of hormone refractory prostate cancer. Both FKBP52 and β-catenin have emerged in recent years as attractive therapeutic targets. The compound MJC13 is a first-in-class drug for targeting the regulation of AR by FKBP52. Through binding a recently identified regulatory surface on AR (BF3), MJC13 prevents the FKBP52-receptor complex from dissociating resulting in the retention of AR in the cytoplasm (De Leon et al. (2011) *Proc Natl Acad Sci USA* 108:11878-83). MJC13 was shown to effectively block AR signaling and AR-dependent cancer cell proliferation in a variety of human prostate cancer cell lines, and preclinical studies demonstrate impressive effects on tumor growth in a prostate cancer xenograft model (Liang et al., (2014) *Pharm Dev Technol*, 1-6; Liang et al. (2014) *American Journal of Modern Chromatography* 1:1-11).

For comparison, other the antiandrogen drugs act as classic anti-androgens through binding the hormone binding pocket. Some antiandrogens prevents AR from entering the nucleus of the cell. This unique mechanism of action has propelled some antiandrogens to the forefront of the prostate cancer drug market in a very short period of time. MJC13 also prevents AR from entering the nucleus. However, MJC13 is unique in that it targets an alternative surface on AR. This "indirect AR targeting" should bypass the partial agonistic effects that result from targeting the hormone binding pocket. In addition, targeting this alternative surface should not be affected by disease resistance to antiandrogens. Thus, MJC13 offers both the positive properties of inhibiting nuclear translocation and prevention of undesirable side effects associated with targeting the AR hormone binding pocket.

SUMMARY

While the rationale for the use of MJC13 in the treatment of prostate cancer follows from the compounds mechanism of action, recent findings strongly suggest that MJC13 will have utility in the treatment of breast cancer patients as well.

In breast cancer (BC), AR is even more widely expressed than estrogen receptor alpha (ER) or progesterone receptor (PR), and can be used to refine breast cancer (BC) classification (Guedj et al. (2012) *Oncogene* 31:1196-1206; Lehmann et al. (2011) *J Clin Invest* 121:2750-67). In women enrolled in the Nurses' Health Study, 77% of 2171 invasive BC were positive for AR by immuno-histochemistry (IHC) (Collins et al. (2011) *Mod Pathol* 24:924-31). Among the subtypes, 88% of ER+, 59% of HER2+, and 32% of triple negative BC (TNBC), which are ER-/PR-/HER2-, were positive for AR (Collins et al. (2011) *Mod Pathol* 24:924-31). Patients with tumors positive for ER, PR, and AR have a longer disease-free survival than tumors that lack all three receptors (Kuenen-Boumeester et al. (1996) *Eur J Cancer* 32A:1560-65), likely because receptor positivity is associated with a well-differentiated state (Park et al. (2010) *Ann Oncol* 21:488-92) and more indolent disease (Hu et al. (2011) *Clin Cancer Res* 17:1867-74) than that of receptor negative tumors. However, AR is an independent predictor of axillary metastases (Agoff et al. (2003) *Am J Clin Pathol* 120:725-31; Soreide et al. (1992) *Eur J Surg Oncol* 18:112-18). Historically, AR and androgens were thought to be protective in breast cancer. However, the studies that suggested a protective effect were generated by combining androgens with estrogen, mimicking the hormonal milieu in premenopausal women. In postmenopausal women, where the majority of ER+BC occurs, particularly those with ER+BC being treated with aromatase inhibitors (AI), there is very little circulating estradiol (E2) because the ovaries are no longer functioning and the AI shuts down aromatase, blocking the conversion of androgens to estrogens in adipocytes and other peripheral tissues. Indeed, circulating levels of androgens (testosterone, androstenedione, and dehydroepiandrosterone-sulfate (DHEA-S)) increase in women on AI therapy (Gallicchio et al. (2011) *Breast Cancer Res Treat*) when conversion of androgens to estrogens is blocked. Further, elevated circulating androgen levels are associated with an increased risk of BC in postmenopausal women (Cauley et al. (1999) *Ann Intern Med* 130:270-77; Zeleniuch-Jacquotte et al. (2012) *Breast Cancer Res* 14:R32). The inventors contemplate that, just as ER serves as a very effective therapeutic target despite being a positive prognostic indicator, so does AR.

Certain embodiments are directed to methods of treating androgen receptor positive breast cancer comprising administering to a subject having breast cancer a therapeutically effective amount of a compound having a chemical structure of Formula I. In certain aspects the method optionally includes administering enzalutamide in combination with the compound of Formula I.

Formula I

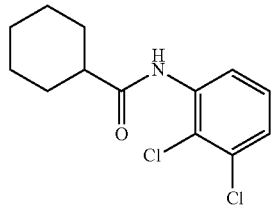

(MJC13)

In certain aspects the androgen receptor to estrogen receptor ratio in the breast cancer cells is greater than 1.3, 2, 4, 6, 8, 10, 50, 100 or more. In certain aspects the subject is male. In still a further aspect the subject is a female and in particular instances is a post-menopausal female. In still a further aspect the subject has been treated or is being treated with aromatase inhibitor therapy. In certain aspects the aromatase inhibitor is anastrozole, exemestane, or letrozole. The methods described herein can further comprise administering an effective amount of anti-estrogen to the subject, e.g., tamoxifen or fulvestrant. In certain aspect the anti-estrogen therapy can be used in combination with enzalutamide. In further aspects the anti-estrogen therapy can be used to treat an enzalutamide resistant cancer or patient. In certain aspects the method can further comprise surgical resection, or administering a chemotherapy or radiation treatments.

As used herein, the term "IC50" refers to an inhibitory dose that results in 50% of the maximum response obtained.

The term "effective amount" means an amount effective, at dosages and for periods of time necessary, to achieve the desired therapeutic or prophylactic result.

An "effective amount" of an anti-cancer agent in reference to decreasing cancer cell growth, means an amount capable of decreasing, to some extent, the growth of some cancer or tumor cells. The term includes an amount capable of invoking a growth inhibitory, cytostatic and/or cytotoxic effect and/or apoptosis of the cancer or tumor cells.

A "therapeutically effective amount" in reference to the treatment of cancer, means an amount capable of invoking one or more of the following effects: (1) inhibition, to some extent, of cancer or tumor growth, including slowing down growth or complete growth arrest; (2) reduction in the number of cancer or tumor cells; (3) reduction in tumor size; (4) inhibition (i.e., reduction, slowing down, or complete stopping) of cancer or tumor cell infiltration into peripheral organs; (5) inhibition (i.e., reduction, slowing down, or complete stopping) of metastasis; (6) enhancement of anti-tumor immune response, which may, but is not required to, result in the regression or rejection of the tumor, or (7) relief, to some extent, of one or more symptoms associated with the cancer or tumor. The therapeutically effective amount may vary according to factors such as the disease state, age, sex and weight of the individual and the ability of one or more anti-cancer agents to elicit a desired response in the individual. A "therapeutically effective amount" is also one in which any toxic or detrimental effects are outweighed by the therapeutically beneficial effects.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; or ameliorate or alleviate the symptoms of the disease caused by the cancer.

The term half maximal effective concentration (EC50) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living mammalian organism, such as a human, monkey, cow, sheep, goat, dogs, cat, mouse, rat, guinea pig, or species thereof.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
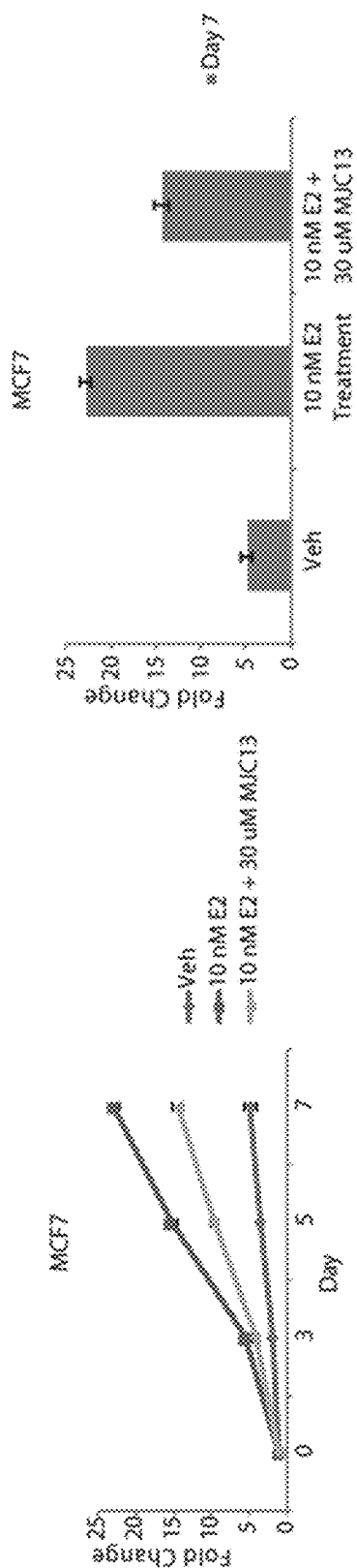
FIG. 1. MJC13, an inhibitor of AR nuclear translocation, inhibits E2-induced proliferation in MCF-7 breast cancer cells.

Breast cancer (BC) is a heterogeneous disease whose clinical outcome is difficult to predict and treatment is not as adapted as it should be. BC can be defined at the clinical, histological, cellular, and molecular levels. Initial studies using DNA microarrays have identified five major BC molecular subtypes (luminal A and B, basal, ERBB2-overexpressing and normal-like) (Perou et al. *Nature* 2000; 406:747-52; Sorlie et al. *Proc Natl Acad Sci USA* 2001; 98:10869-74; Sorlie et al. *Proc Natl Acad Sci USA* 2003; 100:8418-23; Bertucci et al. *Cancer Res* 2005; 65:2170-8). These subtypes, which are defined by the specific expression of an intrinsic set of almost 500 genes, are variably associated with different histological types and with different prognosis. Luminal A BCs, which express hormone receptors, have an overall good prognosis and can be treated by hormone therapy. ERBB2-overexpressing BCs, which overexpress the ERBB2 tyrosine kinase receptor, have a poor prognosis and can be treated by targeted therapy using trastuzumab or lapatinib (Geyer et al. *N Engl J Med* 2006, 355:2733-43; Hudis *N Engl J Med* 2007, 357:39-51). No specific therapy is available against the other subtypes although the prognosis of basal and luminal B tumors is poor. This biologically relevant taxonomy remains imperfect since clinical outcome may be variable within each subtype, suggesting the existence of unrecognized subgroups.

The vast majority (84-91%) of ER+ breast cancers are positive for AR (Kuenen-Boumeester et al. (1996) *Eur J Cancer* 32A:1560-65; Hu et al. (2011) *Clin Cancer Res* 17:1867-74; Soreide et al. (1992) *Eur J Surg Oncol* 18:112-18). In ER+ breast cancers adjuvant treatment with tamoxifen or AIs is generally effective for inhibiting disease progression. However, ~30% of all ER+ tumors display de novo resistance to traditional endocrine therapies and ultimately all metastatic ER+ breast cancers acquire resistance (Bergh et al. (2012) *J Clin Oncol*; Mouridsen et al. (2003) *J Clin Oncol* 21:2101-09). Importantly, circulating levels of androgens (testosterone, androstenedione, and dehydroepiandrosterone-sulfate (DHEA-S)) increase in women on AI therapy (Gallicchio et al. (2011) *Breast Cancer Res Treat*), and AR overexpression increases tamoxifen resistance in BC models in vitro and in vivo (De Amicis et al. (2010) *Breast Cancer Res Treat* 121:1-11). AR and ER directly interact (Migliaccio et al. (2000) *Embo J* 19:5406-17; Panet-Raymond et al. (2001) *Neurotox Res* 3:259-75), bind to common enhancer and promoter regions (Need et al. (2012) *Mol Endocrinol* 26:1941-52; Peters et al. (2009) *Cancer Res* 69:6131-40; Robinson et al. (2011) *Embo J* 30:3019-27), and both utilize FOXA1 as a pioneer factor (Robinson et al. (2011) *Embo J* 30:3019-27). There is substantial genomic and transcriptional overlap between AR and ER signaling in ER+/AR+ MCF7 BC cells (Need et al. (2012) *Mol Endocrinol* 26:1941-52). In fact, liganded AR and ER bind to many of the same sites on DNA, with 26% of ER target genes and 15% of AR targets significantly affected by co-treatment with the opposite hormone (Robinson et al. (2011) *Embo J* 30:3019-27). Interestingly, in ER−/AR+ MDA-MB-453 BC cells, AR binding sites were more similar to ER binding in MCF7 cells than AR in prostate cancer cells (Robinson et al. (2011) *Embo J* 30:3019-27), suggesting that AR can actually substitute for ER in ER negative disease. ER requires FOXA1 to mediate chromatin interactions (Hurtado et al. (2011) *Nat Genet* 43:27-33; Carroll et al. (2005) *Cell* 122:33-43; Zhang et al. (2010) *J Biol Chem* 285:28604-13) and FOXA1 is actually utilized as a "pioneer factor" by both ER and AR (Lupien and Brown (2009) *Endocr Relat Cancer* 16:381-89). It has be discovered that in ER+BC examined pre- and post-neoadjuvant endocrine therapy, responsive tumors showed decreased AR transcript and protein with treatment, while in nonresponsive tumors, AR either increased or remained unchanged (Harvell et al. (2008) *Breast Cancer Res Treat*; Harvell et al. (2008) *Breast Cancer Res Treat*). Recently, additional evidence has emerged that AR plays a role in resistance to AIs (Rechoum et al. (2014) *Breast Cancer Res Treat* 147:473-85). A high ratio of percent cells positive for AR versus ER predicts poor response to tamoxifen (Cochrane et al. (2014) *Breast Cancer Res* 16:R7). Based on these findings it is likely that particularly under the selective pressure of anti-estrogens, or in cases of extremely low estrogen (such as post-menopausal women on AI therapy), acquired resistance to ER-directed therapies results from tumor cells switching from estrogen- to androgen-dependence.

Given the controversy regarding whether androgens are protective or proliferative, studies were undertaken to determine how BC cell lines respond to the non-aromatizable androgen, dihydrotestosterone (DHT), under conditions containing little to no E2 (to mimic post-menopausal women with BC on AI), and whether the new generation anti-androgens could block proliferation of ER+AR+BC lines. It was found that (1) DHT stimulates proliferation of ER+AR+ BC lines in vitro, and (2) new generation anti-androgens inhibit DHT-mediated stabilization of AR and inhibits ligand-mediated nuclear translocation of AR (Cochrane et al. (2014) *Breast Cancer Res* 16:R7). Indeed new generation anti-androgens inhibit DHT-mediated tumor growth of AR+ER+ xenografts (MCF7) and an ER negative BC line (MDA-MB-453) in vivo and inhibits nuclear localization AR in vivo in xenograft tumors (Cochrane et al. (2014) *Breast Cancer Res* 16:R7). An unexpected, but intriguing finding was that new generation anti-androgens also inhibit estrogen-mediated proliferation of ER+/AR+BC cell lines in vitro and indeed, it inhibits tumor growth as effectively as tam in vivo (Cochrane et al. (2014) *Breast Cancer Res* 16:R7). This was surprising because the drug does not bind ERα or β in competitive ligand binding assays (Cochrane et al. (2014) *Breast Cancer Res* 16:R7). Since new generation anti-androgens and tamoxifen work by different mechanisms, Studies were designed to test for a synergistic ability to oppose E2-driven proliferation in ER+/AR+ cell lines using multiple doses of both drugs and found that new generation anti-androgen synergizes with both tam and fulvestrant in vitro and they have now tested the new generation anti-androgen and tam combined versus either alone in E2 treated mice, and the combination was superior to either drug alone. The aforementioned rationale and these data firmly establish AR as a relevant drug target in BC and set the stage for the development of anti-AR targeted therapies as novel strategies for the treatment of BC.

Figure 2:
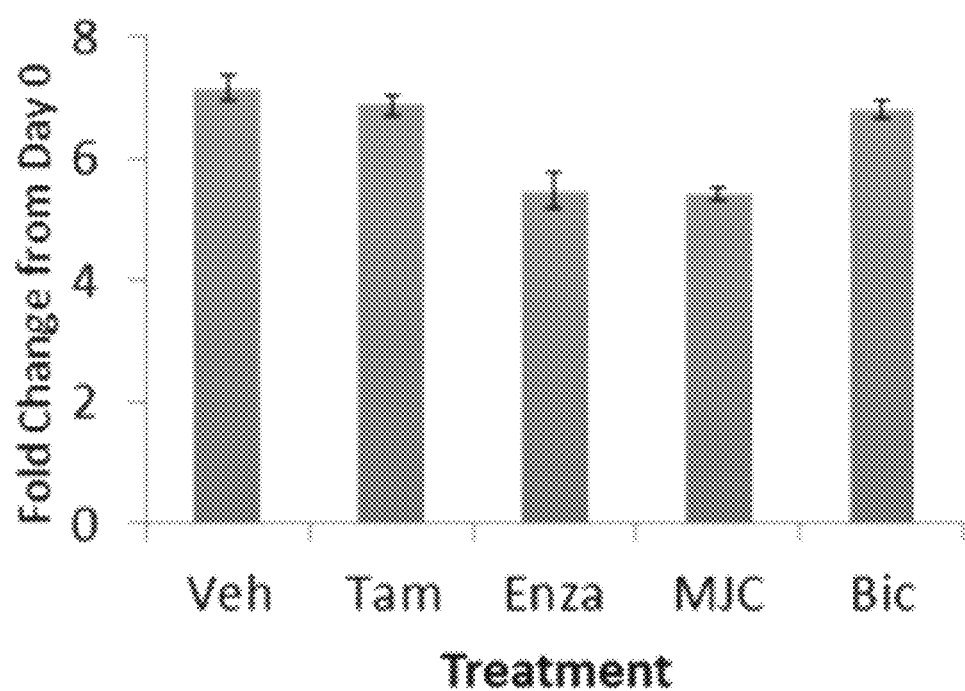
FIG. 2. MJC13 inhibits proliferation in tamoxifen-resistant MCF-7 breast cancer cells.
Figure 3:
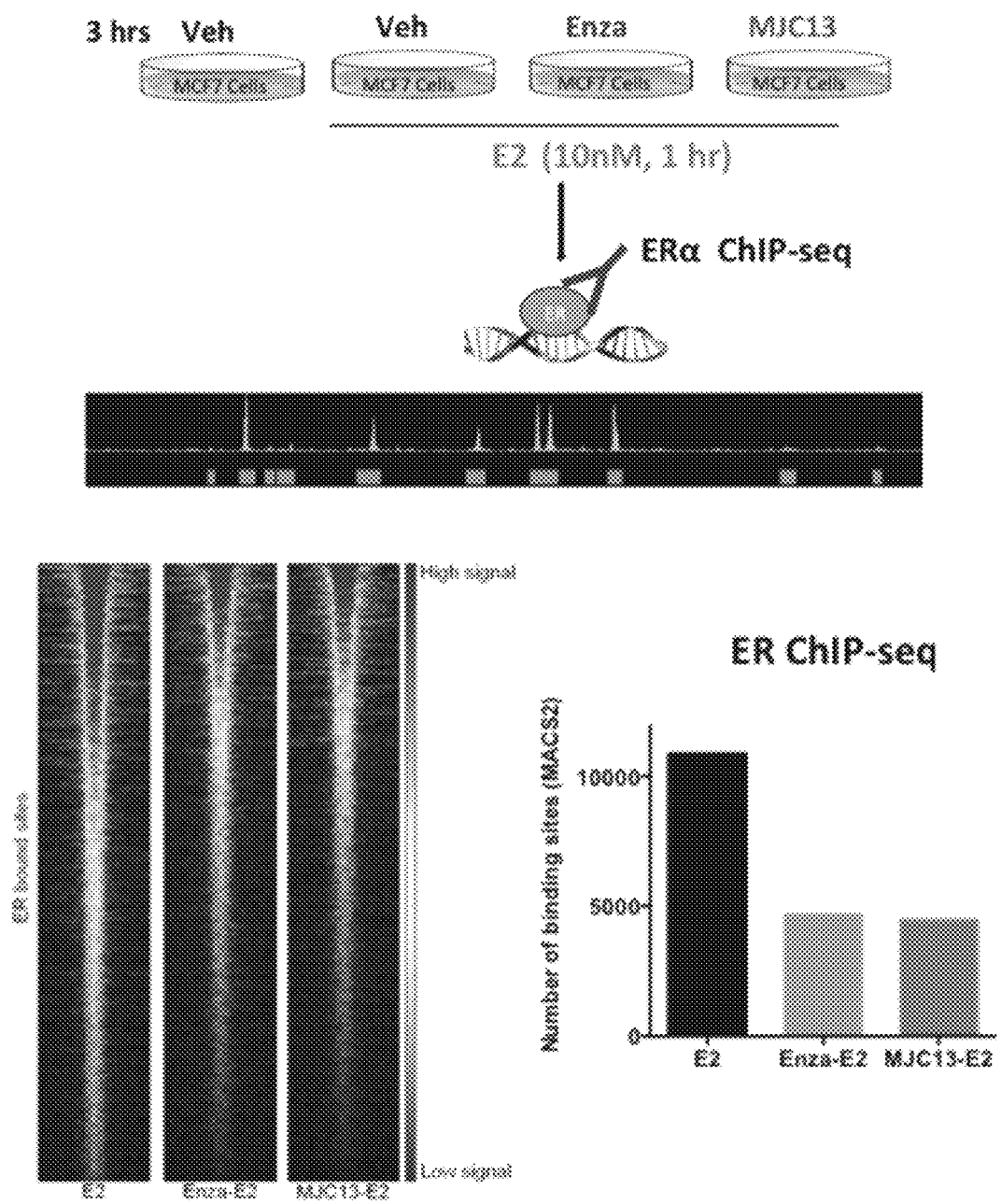
FIG. 3. MJC13 significantly decreases E2-induced ER chromatin binding.

The inventors contemplate that MJC13 would be effective in the treatment of BC. The inventors have demonstrated that MJC13 is an effective inhibitor of E2-induced BC cell proliferation (FIG. 1). In a tamoxifen-resistant model of BC in which there is no difference in AR expression levels MJC13 effectively inhibits cell proliferation (FIG. 2). Finally, the inventors have demonstrated that MJC13 affects ER recruitment to E2-dependent promoters (FIG. 3). The inventors conclude that MJC13 is an attractive candidate drug for the treatment of BC.

I. Therapeutic Compositions Comprising MJC13 and Enzalutamide

Both FKBP52 and β-catenin have emerged in recent years as attractive therapeutic targets. MJC13 represents a first-in-class drug for targeting the regulation of AR by FKBP52. Through binding a recently identified regulatory surface on AR (BF3), MJC13 prevents the FKBP52-receptor complex from dissociating resulting in the retention of AR in the cytoplasm. MJC13 was shown to effectively block AR signaling and AR-dependent cancer cell proliferation in a variety of human prostate cancer cell lines, and preliminary preclinical studies demonstrate impressive effects on tumor growth in a prostate cancer xenograft model.

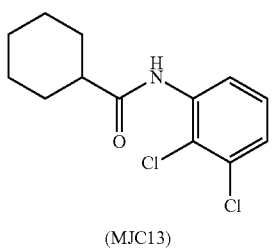

Formula I (MJC13)

MJC13 is described as an inhibitor of FKBP52-regulated AR activity (De Leon et. al. 2011. *PNAS.* 108(29): 11878-83) by targeting the AR BF3 surface. A novel mechanism is disclosed by which FKBP52 and β-catenin interact to co-regulate AR activity in prostate cancer cells. Data indicates that MJC13 targeting to the AR BF3 surface abrogates β-catenin interaction with AR. The FKBP52 proline-rich loop is critical for FKBP52/β-catenin co-regulation of AR activity, and that drugs that disrupt interactions at the proline-rich loop would effectively block FKBP52/β-catenin/AR interactions.

Enzalutamide is an androgen receptor signaling inhibitor. The chemical name is 4-{3-[4-cyano-3-(trifluoromethyl)phenyl]-5,5-dimethyl-4-oxo-2-sulfanylideneimidazolidin-1-yl}-2-fluoro-N-methylbenzamide. The structural formula is:

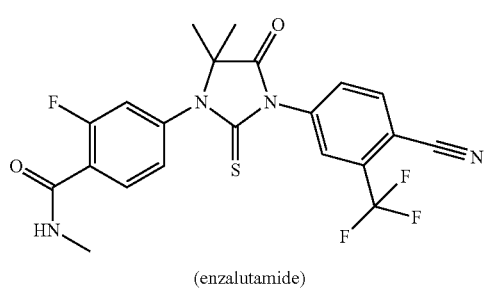

Formula II (enzalutamide)

Enzalutamide is used as an agent for treating castration-resistant prostate cancer who have received docetaxel therapy; enzalutamide also is disclosed for treating breast cancer, prostate cancer, benign prostate hyperplasia and ovarian cancer; See, e.g., U.S. Pat. No. 7,709,517.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids, and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

Additional examples of pharmaceutically acceptable salts and their methods of preparation and use are presented in Handbook of Pharmaceutical Salts: Properties, Selection and Use (2002).

II. Methods for Treating

Described herein are methods and compositions related to treating or reducing the recurrence of breast cancer (BC). In certain aspects the BC is an androgen receptor (AR) positive BC. Certain embodiments are directed to methods of treating the occurrence or reducing the recurrence of BC in a subject, comprising administering to the subject an effective amount of an MJC13 or Enza compound alone or in combination with other BC therapies. In a further aspect, the methods include administering to the subject an effective amount of MJC13, Enza, or MJC13 and Enza to inhibit or reduce proliferation of BC cells, wherein the subject is identified as having or is at risk for occurrence or recurrence of BC. In certain aspects the subject is suspected of having or identified as having a BC that is resistant to ER-directed therapies.

Breast cancer is a proliferative disorder characterized by abnormal cell growth that originates in the breast of males or females. A proliferative disorder refers to any cellular disorder in which the cells proliferate more rapidly than normal tissue growth. A proliferative disorder includes, but is not limited to, neoplasms, which are also referred to as tumors.

As used herein, treating breast cancer includes preventing, precluding, delaying, averting, obviating, forestalling, stopping, or hindering the onset, incidence, or severity of breast cancer or the recurrence of breast cancer in a subject. As used herein, recurrence of breast cancer means the reappearance of one or more clinical symptoms of breast cancer after a period devoid of one or more clinical symptoms of breast cancer. The disclosed method is considered to reduce the occurrence or recurrence of breast cancer if there is a reduction or delay in onset, incidence or severity of the reappearance of breast cancer, or one or more symptoms of breast cancer in a subject at risk for occurrence or recurrence of breast cancer. The disclosed method is also considered to reduce the recurrence of breast cancer if there is a reduction or delay in onset, incidence or severity of the reappearance of breast cancer, or one or more symptoms of breast cancer in a subject at risk for recurrence of breast cancer after receiving a breast cancer therapy. Thus, the reduction or delay in onset, incidence or severity of recurrence of breast cancer can be about a 10, 20, 30, 40, 50, 60, 70, 80, 90, 100%, or any amount of reduction in between.

As used throughout, the term subject refers to a mammal. In certain aspects subject refers to a human. The term subject includes domesticated animals and laboratory animals. Veterinary uses and formulations are contemplated. As used herein, a subject at risk for recurrence of breast cancer is a subject that is at risk for the reappearance of breast cancer after treatment for breast cancer or after remission from breast cancer. A subject having breast cancer is a subject that has been diagnosed with breast cancer, e.g., by using standard clinical methodologies.

Current treatment methods for breast cancer include, but are not limited to, mastectomy, anti-estrogen therapy, radiation therapy, chemotherapy, or combinations of these treatment methods. After treatment, a subject can be monitored for recurrence of breast cancer. Routine follow up visits after treatment allow one of skill in the art to determine if the subject is devoid of clinical symptoms or if clinical symptoms of breast cancer have reappeared. Imaging techniques, such as X-rays, MRIs, CT scans and bone scans can also be used. Lymph node examinations and biopsies can also be utilized to identify a subject at risk for recurrence of breast cancer. These techniques can also be used to stage any recurrence of breast cancer.

Certain aspects are directed to methods of reducing breast tumor progression in a subject, comprising administering to the subject an effective amount of an MJC13 and/or Enza as described herein. This method can be performed in combination with anti-estrogen or aromatase inhibition therapy.

As used herein, reducing breast tumor progression means a method of preventing, precluding, delaying, averting, obviating, forestalling, stopping, or hindering a breast tumor progression in a subject. The disclosed method is considered to reduce breast tumor progression if there is a reduction or delay in breast tumor growth, metastasis, or one or more symptoms of breast cancer in a subject with a breast tumor. The disclosed method is also considered to reduce breast tumor progression if there is a reduction or delay in breast tumor growth, metastasis or one or more symptoms of breast cancer in a subject with a breast tumor after receiving MJC13 and/or Enza as compared to the subject's progression prior to receiving treatment. Thus, the reduction or delay in breast tumor(s) can be about a 10, 20, 30, 40, 50, 60, 70, 80, 90, 100%, or any amount of reduction in between.

III. Formulations and Administration

The agents described herein can be provided in a pharmaceutical composition. Depending on the intended mode of administration, the pharmaceutical composition can be in the form of solid, semi-solid, or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, or other material well known in the art for use in pharmaceutical formulations. The choice of a carrier for use in a composition will depend upon the intended route of administration for the composition. The preparation of pharmaceutically acceptable carriers and formulations containing these materials is described in, for example, Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or combinations thereof include capsules, tablets, pills, powders, and granules. In such solid dosage forms, the compounds described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

In certain embodiments the MJC13 composition can be formulated as described in U.S. Patent publication 2016/0030369, which is incorporated herein by reference.

Administration can be carried out using therapeutically effective amounts of the agents described herein for periods of time effective to treat breast cancer or reduce recurrence of breast cancer. The effective amount may be determined by one of ordinary skill in the art and includes exemplary dosage amounts for a mammal of from about 0.5, 1, 10 to about 200, 500, 1000 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the physician as needed, e.g., in the event of any contraindications. Dosages can vary, and can be administered in one or more dose administrations daily, for one or several days. Guidance can be found in the literature for appropriate dosages for given classes of pharmaceutical products.

Any appropriate route of administration may be employed, for example, parenteral, intravenous, subcutaneous, intramuscular, intraventricular, intracorporeal, intraperitoneal, or oral administration. Administration can be systemic or local. Pharmaceutical compositions can be delivered locally to the area in need of treatment, for example by topical application or local injection. Multiple administrations and/or dosages can also be used. Effective doses can be extrapolated from dose-response curves derived from in vitro or animal model test systems.

Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of treating.

The disclosure also provides a pharmaceutical pack or kit comprising one or more containers filled with one or more of the ingredients of the pharmaceutical compositions. Instructions for use of the composition can also be included.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. A therapeutic method comprising administering to a postmenopausal subject having estrogen receptor positive (ER+) and androgen receptor positive (AR+) breast cancer a therapeutically effective amount of enzalutamide and a compound having a chemical structure of Formula I

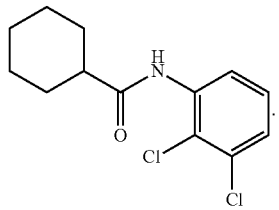

Formula I

2. The method of claim 1, wherein the androgen receptor to estrogen receptor ratio in the breast cancer cells is greater than 2.

3. The method of claim 1, wherein the subject has been treated or is being treated with aromatase inhibitor therapy.

4. The method of claim 3, further comprising administering an effective amount of anti-estrogen to the subject.

5. The method of claim 4, wherein the anti-estrogen is tamoxifen or fulvestrant.

6. The method of claim 1, further comprising administering chemotherapy or radiation treatments.

* * * * *

UNITED STATES PATENT AND TRADEMARK OFFICE
CERTIFICATE OF CORRECTION

| | | |
|---|---|---|
| PATENT NO. | : 10,434,075 B2 | Page 1 of 1 |
| APPLICATION NO. | : 15/623775 | |
| DATED | : October 8, 2019 | |
| INVENTOR(S) | : Marc B. Cox and Jennifer Richer | |

It is certified that error appears in the above-identified patent and that said Letters Patent is hereby corrected as shown below:

In the Specification

Please replace Column 1, Lines 14-18 with the following:
This invention was made with government support under W81XWH-13-0090 awarded by the Medical Research and Development Command, and CA187733 awarded by the National Institutes of Health. The government has certain rights in the invention.

Signed and Sealed this
Twelfth Day of December, 2023

Katherine Kelly Vidal
*Director of the United States Patent and Trademark Office*